United States Patent [19]

Chen et al.

[11] Patent Number: 4,589,896
[45] Date of Patent: May 20, 1986

[54] PROCESS FOR SEPARATING $CO_2$ AND $H_2S$ FROM HYDROCARBONS

[75] Inventors: Michael S. K. Chen, Zionsville; Stephen P. Goff, Kutztown; James VanOmmeren, Werley's Corner, all of Pa.

[73] Assignee: Air Products and Chemicals, Inc., Allentown, Pa.

[21] Appl. No.: 695,582

[22] Filed: Jan. 28, 1985

[51] Int. Cl.[4] .............................................. F25J 3/02
[52] U.S. Cl. ........................................ 62/28; 55/68; 55/73; 62/30; 210/640
[58] Field of Search ............... 210/640; 55/68, 73, 55/158; 62/23–34, 14, 15

[56] References Cited

U.S. PATENT DOCUMENTS

| | | | |
|---|---|---|---|
| 4,130,403 | 12/1978 | Cooley et al. | 55/16 |
| 4,264,338 | 4/1981 | Null | 55/16 |
| 4,318,723 | 3/1982 | Holmes et al. | 62/20 |
| 4,370,156 | 1/1983 | Goddin et al. | 62/17 |
| 4,374,657 | 2/1983 | Schendel et al. | 62/19 |
| 4,435,191 | 3/1984 | Graham | 55/16 |
| 4,444,571 | 4/1984 | Matson | 55/73 |
| 4,466,946 | 8/1984 | Goddin et al. | 423/228 |

OTHER PUBLICATIONS

Clifton S. Goddin, Comparison of Processes for Treating Gases w/High $CO_2$ Content GPA Convention, Mar. 15–17, 1982, Dallas, Texas.

Primary Examiner—Frank Sever
Attorney, Agent, or Firm—Mark L. Rodgers; E. Eugene Innis; James C. Simmons

[57] ABSTRACT

The present invention involves a process for separating components of a feed gas containing acid gases and hydrocarbons to form a $CO_2$-rich stream, an $H_2S$-rich stream and a hydrocarbon-rich stream. Separation is achieved by initially passing the feed gas through a plurality of membrane separation units to produce a hydrocarbon stream and an acid gas stream. The acid gas stream undergoes further separation to produce a $CO_2$-rich product stream and an $H_2S$-rich stream. This process is especially adaptable for treating natural gas streams and gas streams resulting from enhanced oil recovery operations.

12 Claims, 1 Drawing Figure

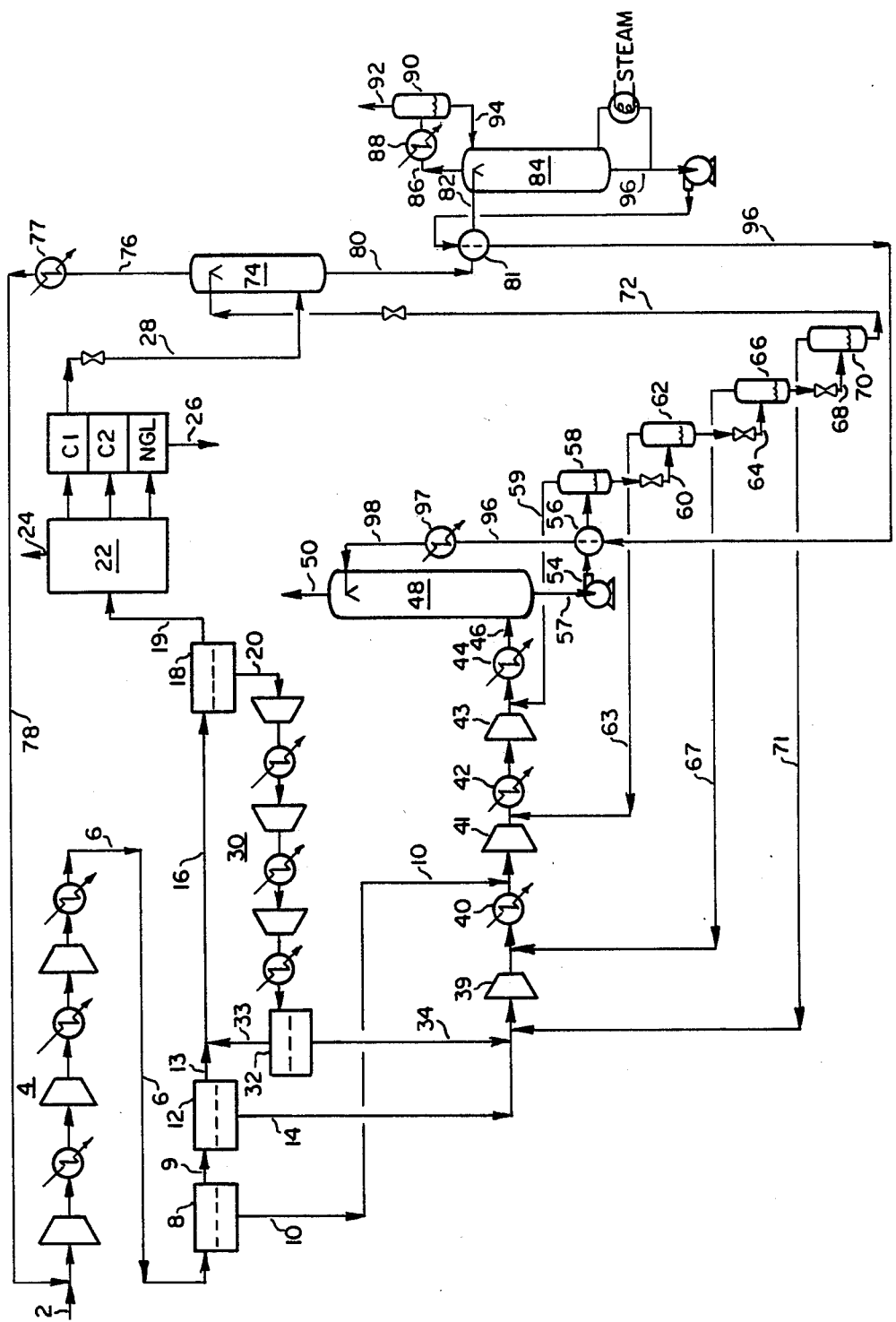

PROCESS FOR SEPARATING $CO_2$ AND $H_2S$ FROM HYDROCARBONS

TECHNICAL FIELD

The present invention relates to separating $CO_2$ and $H_2S$ from hydrocarbons in a gas stream. The invention further involves the subsequent separation of the $CO_2$ from the $H_2S$. This invention is particularly useful in treating natural gas and gas produced from Enhanced Oil Recovery processes.

BACKGROUND OF THE INVENTION

Separating carbon dioxide, hydrogen sulfide and hydrocarbons in streams containing a large percent of carbon dioxide, e.g., as high as 80 or 90 mole%, has become an area of great interest. This interest comes primarily from two areas. One is the recovery of hydrocarbons from naturally occurring gases which were previously thought uneconomical to produce. The second area relates to the increased activity in enhanced oil recovery (EOR). In particular, the use of carbon dioxide for miscible flood is gaining momentum and the associated gas from wells which have been stimulated by this method must be processed at well heads or satellite treating plants.

It is well known that appropriate physical solvents such as propylene carbonate and dimethyl ether of polyethyleneglycol are selective toward acid gas components. A drawback of using physical solvents, however, is that although suitable for bulk $CO_2$ removal, they are not attractive for the above operations because they co-absorb $C_3$ and heavier hydrocarbons.

Suitable chemical solvents which will react with acid gas components are aqueous solutions of potassium carbonates and of amines such as monoethanolomine, diethanolamine, etc. Processes employing these chemical solvents are generally too energy intensive and costly at high $CO_2$ levels.

Several distillation processes have been developed for separating acid gases from hydrocarbons. Two such processes are described in U.S. Pat. Nos. 4,318,723 and 4,370,156. Distillation is effective for bulk $CO_2$ recovery, however, the process must be carried out at cryogenic temperatures in which refrigeration must be provided either by an external means or by expanding part of the compressed gas. Additionally, a large amount of lean oil must be circulated to the tops of the distillation column to prevent $CO_2$ freezing and $CO_2$/ethane azeotrope formation.

Membrane separation units have also been used to separate acid gases from hydrocarbon streams. U.S. Pat. No. 4,130,403 discloses a method wherein a stream from which selected components are to be separated is brought into contact with one side of a permeable membrane. The membrane used, such as a cellulose ester membrane, has permeability constants for $H_2S$ or $CO_2$ of approximately at least $10^{-8}$ (cc)(cm)/(sec)(cm$^2$)(cmHg). Upon contact, the more permeable components of the feed gas will pass through the membrane to a much greater extent than other components, thereby effecting the desired separation. Following contact with the membrane, both the residue stream and the permeate gas stream are separately removed from contact with the membrane.

U.S. Pat. No. 4,374,657 discloses a process for separating acid gases from hydrocarbons by first separating methane from the hydrocarbon stream by a separation method such as low temperature distillation to produce a substantially methane-free hydrocarbon stream containing acid gases, ethane and heavier hydrocarbon components. The substantially methane-free hydrocarbon stream is subsequently passed through a semipermeable membrane system to separate the acid gases from the ethane and heavier hydrocarbons.

Various gas-hydrocarbon separation processes were described by C. S. Goddin in "Comparison of Processes for Treating Gases with High $CO_2$ Content" Annual GPA Convention, Mar. 15-17, 1982. One such process involves using a membrane such as cellulose acetate or polysulfone, to produce a $CO_2$ permeate containing not more than 5 mole% hydrocarbons and a hydrocarbon effluent containing 20 mole% $CO_2$. The latter stream is sent to a conventional DEA unit for final removal of $CO_2$ and $H_2S$. Both the acid gas from the DEA stripper and the sour $CO_2$ permeate are compressed and sent to a Selexol unit for sweetening.

U.S. Pat. No. 4,466,946 describes a method of removing carbon dioxide from a gas stream containing $CO_2$ and hydrocarbons. The gas stream is treated to prevent hydrocarbons from condensing out during $CO_2$ removal. Initial separation can be accomplished by selective permeation of $CO_2$ across a differentially permeable membrane.

Additional processes for separating acid gases from hydrocarbons using semipermeable membranes are described in U.S. Pat. Nos. 4,264,338 and 4,435,191.

BRIEF SUMMARY OF THE INVENTION

The present invention provides for an efficient process for separating components of a feed gas containing $CO_2$, $H_2S$ and hydrocarbons to form a $CO_2$-rich stream, an $H_2S$-rich stream and a hydrocarbon stream.

The feed gas is passed through a plurality of membrane separation units to form a plurality of acid gas-rich permeate streams and a hydrocarbon-rich residual stream. At least one of the acid gas-rich streams is compressed and passed back through at least one membrane separation unit, thereby further removing hydrocarbons from the acid gas-rich stream and forming an additional hydrocarbon-rich stream. The hydrocarbon-rich streams are combined to form a combined hydrocarbon stream having a $CO_2$ concentration of less than 10 mole%. The combined hydrocarbon stream is passed to a natural gas separation plant to form a methane-rich stream and a higher hydrocarbon stream.

The acid gas-rich streams are also combined and subsequently passed to a fractionation column containing an acid gas removal solvent. The solvent selectively absorbs $H_2S$ from the acid gas to form an $H_2S$-rich solvent stream and a $CO_2$ product stream. The $H_2S$-rich solvent stream is passed through a series of flash units to vaporize and remove $CO_2$. The $H_2S$-rich solvent is then passed to an $H_2S$ concentrator where residue $CO_2$ is removed by contact with the methane-rich stream produced above.

The resultant $H_2S$-rich solvent stream is passed to an $H_2S$ stripping column to form an $H_2S$-rich product stream and a regenerated solvent stream which is recycled back to the $H_2S$ absorber.

The $CO_2$ product stream can be used as pipeline gas or in subsequent enhanced oil recovery operations. The $H_2S$-rich product stream is of sufficient purity to be used as a feed to a Claus Plant or similar operation for sulfur recovery. The hydrocarbon product stream is usable as a direct product or can optionally be separated into its individual components in a natural gas liquefaction plant.

BRIEF DESCRIPTION OF THE DRAWING

The single FIGURE is a schematic flow diagram of one embodiment of the present invention.

DETAILED DESCRIPTION OF THE INVENTION

The present invention provides for an improved, energy efficient gas processing system for hydrocarbon recovery from feed gases containing $CO_2$, $H_2S$, and hydrocarbons. Typically the feed gases are naturally occurring gases with a high acid gas concentration, or are the gases produced during enhanced oil recovery (EOR) operations. The advantages of this process include: (1) recovery of as much as 88% of the hydrocarbons in the feed as a hydrocarbon-rich stream, which can subsequently be treated in a conventional processing plant such as a natural gas liquefaction (NGL) plant; (2) production of a $CO_2$-rich stream containing less than 100 ppm, and preferably less than 60 ppm, $H_2S$, such that the stream is suitable for pipelining or reinjecting in an EOR operation; and (3) production of an $H_2S$-rich stream having a concentration of at least 30 mole% $H_2S$ which is suitable for further treatment such as for use in a Claus plant.

A feed gas containing $CO_2$, $H_2S$, and hydrocarbons is compressed and subsequently passed through a plurality of membrane separation units to form an equivalent number of acid gas-rich streams and a hydrocarbon-rich residual stream. Any membrane having different permeabilities for acid gases and hydrocarbons can be used, such as a spiral-wound cellulose-acetate type or polysulfone hollow fiber type. The membrane system separates the bulk of $CO_2$ and essentially all the $H_2S$ from the hydrocarbon residual gas stream.

The membrane system preferably has at least four stages including at least one stage at the front end to make an initial $CO_2$ separation at a high permeate pressure which results in power savings on downstream recompression costs. Additionally at least one stage is positioned such that the permeate stream from the previous stage is contacted with this stage to provide for further separation thereby forming an additional hydrocarbon-rich residual stream. The $CO_2$/$H_2S$-rich permeate streams are withdrawn at different pressure levels to minimize the recompression power. The staged configuration results in increased $CO_2$/$H_2S$ permeation and decreased hydrocarbon loss and membrane cost.

Also, this type of membrane system overcomes the difficulties of $CO_2$ freezing and $CO_2$/ethane azeotrope formation as can occur in a distillation-type process. The overall energy requirement is about 5% lower then the process described in U.S. Pat. No. 4,466,946 which also uses a membrane-solvent system.

The hydrocarbon-rich residual gas streams are combined to form a hydrocarbon-rich stream containing less than 10 mole% $CO_2$. The hydrocarbon-rich stream is subsequently sent to a typical processing unit to separate out at least a portion of the methane and, if desired, other smaller hydrocarbons from the main stream.

The acid gas-rich permeate streams are combined to form a combined acid gas-rich stream which is compressed and subsequently contacted with a solvent capable of removing $H_2S$. The solvent may be a physical solvent which selectively absorbs $H_2S$, or a chemical solvent which reacts with $H_2S$. Examples of appropriate physical solvents include propylene carbonate and the dimethyl ether of polyethylene glycols (sold under the trade name SELEXOL). Examples of suitable chemical solvents are aqueous solutions of potassium carbonates and of amines such as monoethanolamine, diethanolamine, methyl diethanolamine (MDEA), etc.

The $H_2S$ is absorbed to produce a $CO_2$-rich product stream and an $H_2S$-rich solvent stream. The $CO_2$-rich product stream contains less than 100 ppm $H_2S$, and preferably less than 60 ppm $H_2S$, and is suitable for pipelining or for use in EOR operations.

The $H_2S$-rich solvent stream is passed through a series of flash units to vaporize and remove $CO_2$. In most instances, and especially when a physical acid gas removal solvent is used, the series of flash units comprises at least one thermal flash unit and one pressure flash unit. The $CO_2$-rich flash gas is returned to the interstages of the permeate gas compressors for recompression at different pressure levels and subsequent treatment with the solvent.

The $H_2S$-rich solvent stream is subsequently contacted with the methane-rich stream produced above to strip out remaining $CO_2$ to produce a $CO_2$/methane stream and an $H_2S$ concentrated solvent stream. The $CO_2$/methane stream can optionally be recycled back to the initial feed or alternatively treated in an additional process operation.

The $H_2S$ concentrated solvent stream is thermally treated in an $H_2S$ stripping column to remove the $H_2S$ from the solvent to produce an $H_2S$ product stream having an $H_2S$ concentration of at least 30 mole% and preferably at least 35 mole% which is suitable for further treatment; i.e., as feed for a Claus plant for sulfur recovery. The regenerated solvent is suitable for further use and can optionally be recycled to treat the acid gas-rich permeate stream from the membrane system.

One embodiment of the present invention is shown in the accompanying FIGURE. This illustration represents one particular flow scheme and is not meant to limit the scope of the invention. A dehydrated hydrocarbon feed stream 2 of 80 million standard cubic feet/day (MMSCFD) at 35 psia and 43° C. containing 77.4% $CO_2$ and 2004 ppm of $H_2S$, after mixing with a small recycle stream 78, is compressed via a series of compressors and associated heat exchangers 4 to about 740 psia. The compressed feed 6 is passed to a series of membrane units 8, 12 and 18 to form $CO_2$ and $H_2S$-rich permeate streams 10, 14 and 20 respectively and hydrocarbon-rich residual streams 9, 13 and 19. The permeate stream 20 from membrane unit 18 is further compressed in a series of compressors and associated heat exchangers 30 and subsequently passed through an additional membrane unit 32. The residual hydrocarbon-rich stream 33 from this membrane unit 32 is combined with the residual hydrocarbon stream 13 and again passed through membrane unit 18.

The hydrocarbon residual stream 19 from membrane unit 18 is treated in a Natural Gas Liquefaction (NGL) plant to separate the hydrocarbons into methane, ethane, and $C_3+$ hydrocarbons. The hydrocarbons are collected, stream 26, as a combined or as separate products. A small portion of the methane is collected as stream 28 and is used to strip $CO_2$ from $H_2S$-rich solvent. $CO_2$ is removed from the NGL plant as stream 24 and can be collected as useful product or vented to the atmosphere.

The $CO_2/H_2S$-rich permeate stream 34 from membrane 32 is combined with permeate stream 14 and, after mixing with a small recycled flashed gas stream 71, is compressed from 64 to 160 psia in compressor 39 and associated heat exchanger 40. The compressed stream is combined with permeate stream 10 and recycled flashed gas stream 67 and the combined stream is further compressed to 400 psia via compressor 41 and associated heat exchanger 42. The compressed stream is further compressed from 400 to 1000 psia after mixing with another flashed gas stream 63. The final compressed stream is then mixed with a hot flashed gas 59 from thermal flash unit 58, cooled in heat exchanger 44 to remove water and fed, as stream 46, to an $H_2S/CO_2$ fractionation column 48 containing an acid gas removal solvent.

The stream 46 enters the bottom of the fractionation column 48 at 1000 psia and 43° C. containing 96.7% $CO_2$, 2.22% hydrocarbons and 0.755% $H_2S$. The $H_2S$ is removed countercurrently by an acid gas removal solvent in 11 stages. The overhead $CO_2$ stream 50 containing 96% $CO_2$, 3.7% $C_1$ and $C_2$ hydrocarbons, 0.2% $H_2O$ and 52 ppm $H_2S$ is collected as $CO_2$-rich product suitable for EOR reinjection or pipeline transportation or simply venting to the atmosphere.

The $H_2S$-rich solvent leaves the fractionation column as stream 57 at 60° C. containing 61% $CO_2$, 0.93% $H_2S$ and 27% solvent. This stream is heated from 60° C. to 121° C. in heat exchanger 56 with the returning lean solvent stream 96, and is then fed to a thermal flash unit 58. The flashed gas stream 59 from the flash unit 58 is then returned to the fractionation column 48. The solvent is further flashed in three stages, pressure flash units 62, 66, and 70, to remove $CO_2$ and concentrate the dissolved $H_2S$ in the solvent. The $CO_2$-rich gas streams, 63, 67, 71, from the subsequent flash units are recycled and recompressed with the permeate streams entering the $H_2S$ fractionation column 48 as described above. The solvent stream 72 from the flash units is sent to an $H_2S$ concentrator 74 where the solvent is further stripped of $CO_2$ by a small methane stream 28 produced in the NGL plant 22. The overhead gas stream 76 from the $H_2S$ concentrator 74 which contains 62% $CO_2$, 14% $CH_4$, 5% $H_2S$ and 18.5% $H_2O$ is then dehydrated in heat exchanger 77 and recycled to the feed compression system.

The $H_2S$-rich solvent stream 80 is heated with the returning solvent stream 96 in heat exchanger 81 and flashed into the top of an $H_2S$ stripping column 84. The $H_2S$ stripping column 84 has 6 stages and operates at about 35–38 psia and 43° C. to 175° C. At the top of the $H_2S$ stripping column an $H_2S$-rich stream 86 is cooled in heat exchanger 88 and further flashed in flash unit 90. The overhead stripped gas stream 92 leaving the flash unit 90 contains about 35% $CO_2$, 23% $CH_4$, 38% $H_2S$ and 3.7% $H_2O$. This stream 92 is subsequently sent to a Claus or similar treatment plant for sulfur recovery. The hot lean solvent 94 leaves the flash unit 90 and passes through the stripping column 84, after which at least a portion is heated with steam to form a hot lean solvent steam 96. This hot lean solvent stream 96 from the stripper bottom is pumped, cooled in heat exchanger 81, and further cooled in heat exchanger 97 to form cooled solvent stream 98 which is introduced into the $H_2S$ fractionation column 48 to treat the incoming feed.

The process conditions and stream compositions for the particular embodiment described above and depicted in the single FIGURE are set out in Table I below.

TABLE I

| STREAM NUMBER | 2 | 6 | 10 | 14 | 19 | 28 | 34 | 46 |
|---|---|---|---|---|---|---|---|---|
| PRESSURE PSIA | 35.00 | 740.00 | 160.00 | 64.00 | 685.00 | 36.50 | 64.00 | 1000.00 |
| TEMP °C. | 43 | 49 | 49 | 49 | 48 | 43 | 49 | 43 |
| FLOW RATES MOLES/HR | | | | | | | | |
| CARBON DIOXIDE | 6796.70 | 6906.96 | 5055.20 | 1427.33 | 125.74 | 0.10 | 298.68 | 13543.15 |
| METHANE | 1185.50 | 1210.43 | 108.33 | 99.96 | 991.02 | 35.00 | 11.11 | 243.67 |
| ETHANE | 368.80 | 369.44 | 19.73 | 18.12 | 330.52 | 0.10 | 1.08 | 66.49 |
| PROPANE | 219.50 | 219.50 | 0.00 | 0.00 | 219.50 | 0.00 | 0.00 | 0.00 |
| BUTANE | 79.00 | 79.00 | 0.00 | 0.00 | 79.00 | 0.00 | 0.00 | 0.00 |
| PENTANE | 43.90 | 43.90 | 0.00 | 0.00 | 43.90 | 0.00 | 0.00 | 0.00 |
| NITROGEN | 70.20 | 70.24 | 3.90 | 1.94 | 63.46 | 0.05 | 0.95 | 7.04 |
| HYDROGEN SULFIDE | 17.60 | 26.60 | 23.04 | 3.06 | 0.00 | 0.00 | 0.49 | 105.74 |
| SOLVENT | 0.00 | 0.00 | 0.00 | 0.00 | 0.00 | 0.00 | 0.00 | 0.00 |
| WATER | 0.00 | 5.58 | 5.30 | 0.28 | 0.00 | 0.00 | 0.00 | 34.86 |
| COMPOSITION MOLE % | | | | | | | | |
| CARBON DIOXIDE | 77.40 | 77.33 | 96.93 | 92.04 | 6.78 | 0.28 | 95.63 | 96.73 |
| METHANE | 13.50 | 13.55 | 2.08 | 6.45 | 53.48 | 99.29 | 3.56 | 1.74 |
| ETHANE | 4.20 | 4.14 | 0.38 | 1.17 | 17.84 | 0.28 | 0.34 | 0.47 |
| PROPANE | 2.50 | 2.46 | 0.00 | 0.00 | 11.84 | 0.00 | 0.00 | 0.00 |
| BUTANE | 0.90 | 0.88 | 0.00 | 0.00 | 4.26 | 0.00 | 0.00 | 0.00 |
| PENTANE | 0.50 | 0.49 | 0.00 | 0.00 | 2.37 | 0.00 | 0.00 | 0.00 |
| NITROGEN | 0.80 | 0.79 | 0.08 | 0.12 | 3.42 | 0.14 | 0.30 | 0.05 |
| HYDROGEN SULFIDE | 0.20 | 0.30 | 0.44 | 0.20 | 0.00 | 0.00 | 0.16 | 0.76 |
| SOLVENT | 0.00 | 0.00 | 0.00 | 0.00 | 0.00 | 0.00 | 0.00 | 0.00 |
| WATER | 0.00 | 0.06 | 0.10 | 0.02 | 0.00 | 0.00 | 0.00 | 0.25 |
| TOTAL FLOW | | | | | | | | |
| MOL/HR. | 8781.19 | 8931.64 | 5215.49 | 1550.70 | 1853.15 | 35.25 | 312.31 | 14000.93 |
| LB./HR | 349226.62 | 354906.75 | 225794.56 | 65127.60 | 50586.11 | 570.28 | 13398.51 | 606356.06 |
| PHASE | VAPOR | VAPOR | VAPOR | VAPOR | VAPOR | VAPOR | VAPOR | VAPOR |

| STREAM NUMBER | 50 | 57 | 72 | 78 | 80 | 92 | 98 |
|---|---|---|---|---|---|---|---|
| PRESSURE PSIA | 995.00 | 1000.00 | 64.00 | 35.00 | 36.50 | 35.50 | 995.00 |
| TEMP °C. | 70 | 63 | 110 | 43 | 109 | 43 | 43 |
| FLOW RATES | | | | | | | |

TABLE I-continued

| MOLES/HR. | | | | | | | |
|---|---|---|---|---|---|---|---|
| CARBON DIOXIDE | 6691.70 | 6889.83 | 125.16 | 110.20 | 15.04 | 15.04 | 0.00 |
| METHANE | 219.66 | 24.28 | 0.01 | 24.93 | 10.07 | 10.07 | 0.00 |
| ETHANE | 38.43 | 28.29 | 0.71 | 0.64 | 0.17 | 0.17 | 0.00 |
| PROPANE | 0.00 | 0.00 | 0.00 | 0.00 | 0.00 | 0.00 | 0.00 |
| BUTANE | 0.00 | 0.00 | 0.00 | 0.00 | 0.00 | 0.00 | 0.00 |
| PENTANE | 0.00 | 0.00 | 0.00 | 0.00 | 0.00 | 0.00 | 0.00 |
| NITROGEN | 6.79 | 0.25 | 0.00 | 0.04 | 0.00 | 0.00 | 0.00 |
| HYDROGEN SULFIDE | 0.36 | 104.56 | 25.35 | 9.12 | 16.22 | 16.22 | 0.00 |
| SOLVENT | 0.01 | 2999.99 | 2999.30 | 0.00 | 2999.00 | 0.00 | 2999.00 |
| WATER | 15.90 | 1219.06 | 1066.32 | 5.59 | 1033.36 | 1.61 | 1031.75 |
| COMPOSITION MOLE % | | | | | | | |
| CARBON DIOXIDE | 95.97 | 61.15 | 2.97 | 73.21 | 0.37 | 34.88 | 0.00 |
| METHANE | 3.15 | 0.22 | 0.00 | 16.56 | 0.25 | 23.36 | 0.00 |
| ETHANE | 0.55 | 0.25 | 0.02 | 0.43 | 0.00 | 0.40 | 0.00 |
| PROPANE | 0.00 | 0.00 | 0.00 | 0.00 | 0.00 | 0.00 | 0.00 |
| BUTANE | 0.00 | 0.00 | 0.00 | 0.00 | 0.00 | 0.00 | 0.00 |
| PENTANE | 0.00 | 0.00 | 0.00 | 0.00 | 0.00 | 0.00 | 0.00 |
| NITROGEN | 0.10 | 0.002 | 0.00 | 0.03 | 0.00 | 0.01 | 0.00 |
| HYDROGEN SULFIDE | 0.01 | 0.93 | 0.60 | 6.06 | 0.40 | 37.62 | 0.00 |
| SOLVENT | 0.00 | 26.63 | 71.12 | 0.00 | 73.62 | 0.00 | 74.40 |
| WATER | 0.23 | 10.82 | 25.29 | 3.71 | 25.36 | 3.73 | 25.60 |
| TOTAL FLOW | | | | | | | |
| MOL/HR. | 6972.84 | 11266.25 | 4216.71 | 150.52 | 4073.87 | 43.12 | 4030.76 |
| LB./HR. | 299665.06 | 1168043.00 | 863431.56 | 5681.60 | 857780.38 | 1410.46 | 856369.81 |
| PHASE | VAPOR | LIQUID | LIQUID | VAPOR | LIQUID | VAPOR | LIQUID |

A comparison of stream composition and membrane performance between the above embodiment and the process described by Goddin is set out in Table II below.

TABLE II

| | Present Invention Process | Goddin's Permeation System |
|---|---|---|
| 1. Feed Flow lb-mole/hr | 8781.2 | 8040 |
| MMSCFD | 79.87 | 73.13 |
| Composition % | | |
| $CO_2$ | 77.4 | 80.0 |
| $H_2S$ | 2004 ppmv | 1493 ppmv |
| $C_1$ | 13.5 | 9.33 |
| $C_2$ | 4.2 | 3.86 |
| $C_3$ | 2.5 | 3.11 |
| $C_4$ | 0.9 | 1.14 |
| $C_{5+}$ | 0.5 | 0.59 |
| $N_2$ | 0.8 | 1.79 |
| 2. $CO_2$ in HC Residue | 6.8% | 20% |
| 3. $CO_2$ in Permeate | 95.8% | >95% |
| 4. Hydrocarbon Loss | 12.0% | ≈22% |
| 5. $CO_2$ Permeation Rate SCFH/ft$^2$ - 100 psi | 6 | 1.52 |

As can be seen from the above Tables, the present process is an efficient method of the separating and recovering hydrocarbons and $CO_2$ from a feed gas stream resulting from natural gas wells or from enhanced oil recovery operations. In terms of feed $CO_2$ treated the energy equivalent is 41.6 MBTU/lb-mole $CO_2$. The overall hydrocarbon recovery is 88% and the $CO_2$ recovery is 97%. The above described process results in about a 5% decrease in the overall energy requirements as compared to other typical prior art processes. In addition, the present invention has the advantages in that it reduces residual $CO_2$ in the hydrocarbon stream to less than 10% and even as low as 6.8% in the specific example above instead of 20% as in the prior art, and also in reducing the hydrocarbon loss to about 12% instead of the 22% loss in the prior art.

Having thus described the present invention, what is now deemed appropriate for letters patent is set out in the following appended claims.

What is claimed is:

1. A process for separating components of a feed gas containing $CO_2$, $H_2S$ and $C_1$ and higher hydrocarbons to form a $CO_2$-rich stream, an $H_2S$-rich stream and a hydrocarbon-rich stream, said process comprising:
   (a) passing said feed gas to a plurality of membrane separation units to form a plurality of acid gas-rich streams and a hydrocarbon-rich stream;
   (b) compressing at least one acid gas-rich stream and passing said stream back through at least one membrane separation unit to further remove hydrocarbons and thereby form an additional hydrocarbon-rich stream;
   (c) combining said hydrocarbon-rich streams to form a combined hydrocarbon-rich stream containing less than 10 mole% $CO_2$;
   (d) separating said combined hydrocarbon-rich stream to form a methane-rich stream and a higher hydrocarbon-rich stream;
   (e) combining the acid gas-rich streams to form a combined acid gas-rich stream;
   (f) compressing said combined acid gas-rich stream;
   (g) contacting said combined acid gas-rich stream with a solvent capable of absorbing $H_2S$ thereby forming a $CO_2$ product stream containing less than 100 ppm $H_2S$ and an $H_2S$-rich solvent stream;
   (h) passing said $H_2S$-rich solvent stream through a series of flash units to remove $CO_2$ from the $H_2S$-rich solvent stream;
   (i) subsequently contacting the $H_2S$-rich solvent stream with the methane-rich stream in step (d) to further remove $CO_2$; and
   (j) thermally treating the resultant $H_2S$-rich solvent stream to form an $H_2S$-rich product stream having a concentration of at least 30 mole% $H_2S$ and a regenerated solvent stream.

2. The process in accordance with claim 1 wherein the regenerated solvent stream is recycled to absorb $H_2S$ from the combined acid gas-rich stream in step (g).

3. The process in accordance with claim 2 wherein the series of flash units comprises at least one thermal flash unit and at least one pressure flash unit.

4. The process in accordance with claim 3 wherein the solvent capable of absorbing $H_2S$ is a physical acid gas removal solvent.

5. The process in accordance with claim 4 wherein the physical acid gas removal solvent is a mixture of polyethylene glycol dimethyl ethers.

6. The process in accordance with claim 2 wherein the solvent capable of absorbing $H_2S$ is a chemical acid gas removal solvent.

7. The process in accordance with claim 6 wherein the chemical acid gas removal solvent is diethanolamine.

8. The process in accordance with claim 2 wherein the $CO_2$ product stream contains less than 60 ppm $H_2S$.

9. The process in accordance with claim 8 wherein the $H_2S$ product stream has an $H_2S$ concentration of at least 35 mole % $H_2S$.

10. A process for separating components of a feed gas containing acid gases and $C_1$ and higher hydrocarbons to form a $CO_2$-rich stream, an $H_2S$-rich stream and a hydrocarbon-rich stream, said process comprising:
    (a) passing said feed gas to a plurality of membrane separation units to form a plurality of acid gas-rich streams and hydrocarbon-rich stream;
    (b) compressing at least one acid gas-rich stream and passing said stream back through at least one membrane separation unit to further remove hydrocarbons and thereby form an additional hydrocarbon-rich stream;
    (c) combining the hydrocarbon-rich streams, and subsequently passing said combined hydrocarbon stream, containing less than about 10 mole% $CO_2$, to a natural gas processing plant to form a methane-rich stream and a higher hydrocarbon-rich stream;
    (d) combining the acid gas-rich streams and subsequently passing said combined stream through successive step compression to a fractionation column containing a solvent capable of selectively removing $H_2S$ thereby forming an $H_2S$-rich solvent stream and a $CO_2$ product stream containing less than 100 ppm $H_2S$;
    (e) passing said $H_2S$-rich solvent stream through a series of flash units to separate $CO_2$ from the $H_2S$-rich solvent;
    (f) subsequently introducing said $H_2S$-rich solvent stream into an $H_2S$ concentrator where residual $CO_2$ is removed from said solvent stream by contact with the methane-rich stream produced in step (c);
    (g) passing the resultant $H_2S$-rich solvent stream to an $H_2S$ stripping column to form an $H_2S$-rich product stream, having a concentration of at least 30 mole% $H_2S$, and a regenerated solvent stream; and
    (h) recycling said solvent stream back to the $H_2S$ absorption column.

11. The process in accordance with claim 10 wherein the solvent capable of absorbing $H_2S$ is a physical acid gas removal solvent.

12. The process in accordance with claim 11 wherein the series of flash units comprises at least one thermal flash unit and at least one pressure flash unit.

* * * * *